US 6,602,988 B2

(12) United States Patent
Moser et al.

(10) Patent No.: US 6,602,988 B2
(45) Date of Patent: Aug. 5, 2003

(54) CYCLODEXTRIN DIMERS WITH SPACERS HAVING PEPTIDE STRUCTURES FOR ENCAPSULATION OF PHARMACEUTICALLY ACTIVE SUBSTANCES WITH POTENTIAL HIGH SIDE-EFFECTS

(75) Inventors: Jörg G. Moser, Duesseldorf (DE); Ralph Hoffmann, Erkrath (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 167 days.

(21) Appl. No.: 09/760,268

(22) Filed: Jan. 12, 2001

(65) Prior Publication Data

US 2002/0094950 A1 Jul. 18, 2002

(51) Int. Cl.[7] .......................... C07K 1/00; C08B 37/16; A01N 43/04
(52) U.S. Cl. .................. 530/395; 530/350; 530/300; 536/103; 514/2; 514/58; 435/7.5
(58) Field of Search ............................ 536/103; 514/58, 514/2; 435/7.5; 530/395, 350, 300

(56) References Cited

FOREIGN PATENT DOCUMENTS

WO      WO 99/24474      5/1999

OTHER PUBLICATIONS

Moser et al. "Cyclodextrin dimers used to prevent side effects of photochemotherapy and general tumor therapy", J. of Inclusion Phenomena and Molecular Recognition in Chemistry, vol 25, pp 29–34, 1996.*

Ruebner, A. et al J. Incl. Phenon 27, pp. 69–84 (1997).

Antisperger et al. 8th Int. Symposium Cyclodextrins (Butapest) pp. 148–156 (1996).

* cited by examiner

Primary Examiner—Christopher S. F. Low
Assistant Examiner—Rita Mitra
(74) Attorney, Agent, or Firm—BJ Associates; Bolesh J. Skutnik

(57) ABSTRACT

A rigidly spaced, cyclodextrin dimers having a preselected breaking point within the spacer sequence so as to controllably release the active pharmaceutically active substance only after it reaches the desired treatment site is described. These preselected breaking points are stable in blood but are cleavable within cells. In preferred embodiments, the cyclodextrin-pharmaceutically active substance complex is targeted to specific sites via incorporation of specific antibodies for the targeted sites, typically by complexing a biotin-avidin system to specific antibodies which thereby targets the complex to a specific site. Once at the site as the complex is taken up into the cell the preselected break point is cleaved and the encapsulated pharmaceutically active substance becomes available for action within the targeted cell. This approach permits the use of highly effective and efficient pharmaceutically active substances, whose safety restricts use to last chance efforts or which are unable to qualify for human use due to their potential side effects. In a preferred embodiment peptide structures are used as part of the spacers between bridged cyclodextrins The cyclodextrin oligomers are complexed with pharmaceuticals with potential high side effects to safely, efficiently achieve the therapeutic action dsired.

12 Claims, No Drawings

CYCLODEXTRIN DIMERS WITH SPACERS HAVING PEPTIDE STRUCTURES FOR ENCAPSULATION OF PHARMACEUTICALLY ACTIVE SUBSTANCES WITH POTENTIAL HIGH SIDE-EFFECTS

BACKGROUND OF THE INVENTION

1. Field of the Invention

The present invention relates to therapies with pharmaceutically active substances with potentially high side-effects, which have to be transported in the blood and delivered to specific target cells without influencing healthy organs.

2. Information Disclosure Statement

Therapies with very effective pharmaceutically active substances e.g. with antimitotic properties for cancer therapy often suffer from the fact that healthy organs are damaged severely by the therapy. These side effects often make the use of certain therapies impossible even if the therapy would be effective in curing the diseased organ. Therefore it is desirable to achieve specific targeting of the pharmaceutically active substances to the diseased organ or cells, and moreover to inhibit the delivery of the pharmaceutically active substance to healthy organs. Often a localized application of the pharmaceutically active substance to the diseased site is not possible, but the pharmaceutically active substance has to be administered systemically through the blood stream and is accessible for the whole organism. One way to prevent this is to build complexes with carrier molecules that mediate an inert transport through the blood and selectively release the pharmaceutically active substance at the target site.

In patent description in Pat. Ser. No. 09/554,223 by Jörg G. Moser (published as WO 9924474) a method was introduced to detoxify pharmaceuticals with dangerous side effects by physical encapsulation into cyclodextrin [CD] oligomers with a relatively rigid spacer structure B.
Cyclodextrins are annular glucose polymers, which are called alpha, beta or gamma cyclodextrin depending on the number of glucose moieties present, namely for 6, 7 or 8, respectively. A lipophilic cavity exists in the center of a cyclodextrin, where lipophilic substances can be enclosed. This property of cyclodextrins can be used to render hydrophobic substances water soluble. Preferably cyclodextrin oligomers are able to encapsulate hydrophobic substances. The bridging structures or spacers between the cyclodextrins determine the distance between the cavities and thereby the size of the molecule that can be encapsulated. The spacer structures have to be rigid to ensure the correct orientation of the cyclodextrin moieties for the retention of the cavity structure. Therefore the spacer structures contain preferably chemical bonds that cannot rotate freely.

The protected molecule is released upon cleavage of either the cyclodextrins or the bridging structures between the cyclodextrins. The necessary destruction of the complex and the consequent liberation of the included pharmaceutically active substance at the target site can be effected easily by hydrolysis of the cyclodextrin by a specific enzyme (Moser Ser. '223) or preferably by destruction of the spacer B'. In both cases the affinity between pharmaceutically active substance and covering CD's ceases by 4 orders of magnitude, and the pharmaceutically active substance slips out of the complex into the next living cell. The synthesis of CD-dimers is well known (See, for example A. Rübner et al. J. Inclin. Phenom. 27 69-84 (1997)). Antimitotics like taxanes can be encapsulated this way.

The targeting of the complex to the diseased organ, e.g. a tumor, can be mediated by specific antibodies, preferably by using the biotin-avidin (bAV) system. In particular, it has been tried to couple complexes from CD-dimers and pharmaceuticals with biotin-avidin (bAV) systems in order to connect the complex with biotinylated monoclonal antibodies (b-mAB's) and, thereby, to concentrate the complex specifically to xeno-transplanted tumours in nude mice. In these experiments, the effect was not statistically significant even though the administered concentrations were very high.

Therefore, it is object of the present invention to improve the effect of complexed pharmaceutically active substances by changing the structure of the spacer of the CD dimer in a way that the complex can be concentrated at the desired site and that the pharmaceutically active substance is released intracellularly where its action is mostly efficient. Moreover, inert transport of the pharmaceutically active substance through the blood is possible, contrary to the prior art.

BRIEF SUMMARY OF OBJECTIVES OF THE INVENTION

It is an object of the invention to provide cyclodextrin end capped structures connected by rigid spacer sequence to encapsulate pharmaceutically active substances, where the spacer sequence has a preselected breaking point, which is stable in blood but cleavable within cells.

It is another object of the present invention to use, as spacers, peptide structures that are not cleavable by the proteolytic enzymes in blood but are sensitive to intracellular enzymes.

It is a further object of the present invention to modify the peptide spacer with biotin residues in different positions to couple the complex via a biotin avidin system to specific antibodies and thereby target the complex to specific sites.

Briefly stated, the present invention provides a Rigidly spaced, cyclodextrin dimers having a preselected breaking point within the spacer sequence so as to controllably release the active pharmaceutically active substance only after it reaches the desired treatment site. These preselected breaking points are stable in blood but are cleavable within cells. In preferred embodiments, the cyclodextrin-pharmaceutically active substance complex is targeted to specific sites via incorporation of specific antibodies for the targeted sites, typically by complexing a biotin-avidin system to specific antibodies which thereby targets the complex to a specific site. Once at the site as the complex is taken up into the cell the preselected break point is cleaved within the cell and the encapsulated pharmaceutically active substance becomes available for action within the targeted cell. This approach permits the use of highly effective and efficient pharmaceutically active substances, whose safety restricts use to last chance efforts or which are unable to qualify for human use due to their potential side effects. In a preferred embodiment peptide structures are used as part of the spacers between bridged cyclodextrins The cyclodextrin oligomers are complexed with pharmaceuticals with potential high side effects to safely, efficiently achieve the therapeutic action desired.

The above and other objects, features and advantages of the present invention will become apparent from the following detailed description.

DETAILED DESCRIPTION OF PREFERRED EMBODIMENTS

The essential element of the present invention is the provision of a preselected breaking point, which is stable in blood but cleavable within specific cells, in a system capable of transporting hydrophobic moieties through the blood stream. Once a targeted cell site is reached, the carrier system cleaves to provide access of the hydrophobic pharmaceutically active substance moiety in the cell to initiate therapeutic action as required by the medical treatment. Since the blood contains several proteolytic enzymes the breaking point is selected to only be sensitive to intracellular enzymes. The structure of the carrier system is preferably a cyclodextrin (CD) dimer with a rigid spacer separating the CD ends, wherein the length and other properties of the spacer are selected to allow capture and retention of a pharmaceutically active substance within the cavity formed between the ends. The preselected breaking point preferably is in the spacer structure along with moieties which may target the desired cell sites, where therapeutic action is required.

When a peptide structure is used as a spacer structure with breaking point, free lysine has to be avoided due to the frequent trypsin-like specificity of blood proteases. Intracellular proteases of the proteasomes contain chymotrypsin. A compatible sequence for the spacer is e.g.:

(I) (6-biotinyl)CD-Tyr-Asp-aminopropyl amideo-CD(6-biotinyl)

↑

The preselected breaking point is labelled by the arrow (↑). Sequence (I) would have a length between the CD moieties of 6.5 A. The sequence allows connection to a b-mAB system over the avidin or streptavidin. The basic CD, as a 6-biotinylated derivative, is known. Within the spacer sequence, every further amide bond would elongate the spacer length by 2.7 Å, every additional —$CH_2$-group by 1.5 Å.

Therefore, for guest molecules with a greater Van der Waals-distance more amino acids and/or methylene groups (at the CD moieties) can be inserted into the spacer structure. For a distance of 8.5–9.0 Å the following sequence is preferred:

(II) CD-Tyr-Asp-Lys(biotinyl)-aminopropylamido-CD(6-biotinyl)

↑

Minor changes in length are effected by exchange of the propyl- to butyl residue [IIa]. For more extended guest molecules a repeated biotinylation inside the spacer is possible, e.g. an adjacent peptide:

(III)

CD-(βAla)-Tyr-Asp-Lys(biotinyl)-Lys(biotinyl)-aminopropylamide-CD

↑

This complex allows for polyphasic accumulation of a complexed pharmaceutically active substance, e.g. Paclitaxel, at the target site, as just noted Moser Ser. No. 09/554,223, but now the added break point between Tyr-Asp provides easier access to the encapsulated pharmaceutically active substance. The position of the Lys(biotinyl)-residues is variable with respect to the breaking point. The following structure (IV) would be equivalent or better as (III):

(IV)

CD-(βAla)-Lys(biotinyl)-Tyr-Asp-Lys(biotinyl)-aminopropylamido-CD

↑

As control preparations for in vitro experiments the following sequences are suitable:

(II') CD-Tyr-Pro-Lys(biotinyl)-aminopropylamido-CD which cannot be split i.e. does not have a preselected break point; and (II') CD-Tyr-Pro-Lys(Me)-aminopropylamido-CD which can neither be split nor can it be attached to a targeting moiety.

All peptide structures described are found only in proteins with Mr 10exp5 Da (EMBL Data Service), but are uncommon enough to be detected by the ubiquitin system during receptor mediated uptake and so, are split by enzyme activities of the proteasomes. This splitting at the preselected breakpoint results in reduced affinity to the complexed pharmaceutically active substance which is released and thereby activated within the target cell.

EXAMPLES (1) Synthesis of a Peptide Structure With Preselected Breakpoint

The peptide is synthesized according the well known Fmoc-procedure described by M & A Bodanzky in *The Practice ofPeptide Synthesis* (Springer Verlag, Heidelberg, 1984). For sequence (IV) preferably at first Fmoc-Lys(Boc)-OH is fixed on the WANG resin. Afterwards the Fmoc group is split by DMF-Piperidine and, after washing with the sequence DMF-dichloromethane-ethanol-propanol (2), the following amino acids are added as Fmoc-Asp(OtBut)-OH (alternative: Fmoc-Pro-OH), Fmoc-Tyr(OtBut)-OH, and again Fmoc-Lys(Boc)-OH, each by activation with diisopropyl carbodiimide in the presence of dimethylamino pyridine and/or diisopropylethylamide. Finally, carbodiimide-activated acetyl (2)-CD is coupled to the peptide and the complete structure is removed from the resin by trifluoroacetic acid. Afterwards, biotinylation is performed with biotin hydroxysuccininimidyl ester and the (2N) aminopropylamido-CD is coupled to the activated peptide. Preparative thin layer chromatography {Silica gel 60, solvent acetic acid-acetone-methanol-benzene 5:5:20:70 (all by vol.)} is used for isolation with UV or iodine vapor detection, additionally spraying with dimethylamino cinnamic aldehyde or ninhydrin. MALDI serves for Mr-determination and as a purity check. This procedure is applicable without any change to all peptide structures mentioned.

(2) Test on Intactness in Blood Samples (to be Performed Later on Every Patient Blood)

0.1–0.5 mg of the peptide (complete sequence or sequence according to (II)) are admixed to 1 ml of blood serum and incubated at 37° C. for 1–8 hours. Afterwards, the sample is precipitated with perchloric acid, the supernatant neutralized with KOH, and chromatographed analytically as mentioned in example (1). The peptide spot should be unchanged under these conditions, as we found in 22 patient samples.

(3) Inclusion of Paclitaxel or Other Cytostatic Antibiotics in Cyclodextrin Oligomers According to Example (1)

10 $\mu$M of the length-adequate dimer(according example (1)) in watery buffer (HEPES or phosphate pH 7.4) and 10 $\mu$M Paclitaxel [or other cytostatics like colchicine, vincristine, vinblastine as given in Moser (Ser. No. 09/554,223), preferably in DMSO solution, are incubated overnight at 50° C. Monomerization of the pharmaceutically active substances is followed by fluorimetry. Mitotic activity in cell cultures is documented at 40 nM pharmaceutically active substance concentration in the presence and absence of the cyclodextrin oligomer. This solution can be equally prepared and used for treatment of patients as an isotonic infusion.

(4) Conditioning of Tumors in Patients and Application of the Solution According to Example (3)

According to K Bosslet et al. (Die gelben Hefte 32 149–155 (1992)), a tumor in a patient is first labelled (a) by infusion of a tumor-specific or neovascularization-specific humanized biotinylated antibody or antibody fragment or (b) a humanized antibody-chymotrypsin conjugate.

If in case (a) most of the antibody is eliminated from blood (as checked e.g. from biotin content of blood samples), NeutrAvidin is infused at adequate dosage to eliminate remnants of free antibody from the blood and other storage organs (Liver, kidney) and in order to label antibody bound to the tumor. As a 3rd infusion after about one hour up to 2 liters containing up to 20 $\mu$M pharmaceutically active substance/per day according to example (III) are infused to the patient.

Having described the preferred embodiments of the invention, it is to be understood that the present invention is not limited to these precise embodiments, and that various changes and modifications may be effected therein by one skilled in the art without departing from the scope or spirit of the invention as defined in the appended claims.

What is claimed is:

1. A rigidly spaced, cyclodextrin dimer to transport pharmaceutically active substances having potentially substantial side effects comprising:

a spacer sequence to rigidly space the cyclodextrin ends;

said spacer sequence is a peptide structure; and wherein said peptide structure is stable during transport in blood.

2. The rigidly spaced, cyclodextrin dimer according to claim 1, wherein said peptide structure has a preselected break point which is cleavable by intracellular enzymes but not by enzymes in blood.

3. The rigidly spaced, cyclodextrin dimer according to claim 2, wherein said breaking point within said peptide structure consists essentially of the sequence [N]-Tyr-Asp-[C], which is sensitive to chymotrypsin.

4. The rigidly spaced, cyclodextrin dimer according to claim 1, wherein said peptide structure contains Lys (biotinyl) for coupling said spacer sequence to an avidin-biotin system.

5. The rigidly spaced, cyclodextrin dimer according to claim 1, which is complexed with a pharmaceutically active substance.

6. The rigidly spaced, cyclodextrin dimer according to claim 1, wherein said peptide structure contains repeated Lys(biotinyl) moiety in adjacent configuration, providing the possibility to concentrate said moiety by accumulation.

7. The rigidly spaced, cyclodextrin dimer according to claim 5, wherein said peptide structure contains repeated Lys(biotinyl) moiety in adjacent configuration, providing the possibility to concentrate the complex by accumulation.

8. The rigidly spaced, cyclodextrin dimer according to claim 5, wherein said complexed moiety is used in tumor therapy.

9. A medicament containing a cyclodextrin moiety according to claim 1.

10. The rigidly spaced, cyclodextrin dimer according to claim 1, wherein said peptide structure contains repeated Lys(biotinyl) moiety in spacer configuration, providing the possibility to concentrate said moiety by accumulation.

11. The rigidly spaced, cyclodextrin dimer according to claim 5, wherein said peptide structure contains repeated Lys(biotinyl) moiety in spacer configuration, providing the possibility to concentrate the complex by accumulation.

12. A medicament containing a complexed cyclodextrin moiety according to claim 5.

* * * * *